United States Patent [19]

Bien et al.

[11] Patent Number: 4,785,184

[45] Date of Patent: Nov. 15, 1988

[54] INFRARED TRACE ELEMENT DETECTION SYSTEM

[75] Inventors: Fritz Bien, Concord; Lawrence S. Bernstein, Bedford; Michael W. Matthew, Burlington, all of Mass.

[73] Assignee: Spectral Sciences, Inc., Burlington, Mass.

[21] Appl. No.: 866,891

[22] Filed: May 27, 1986

[51] Int. Cl.$^4$ .......................................... G01N 21/61
[52] U.S. Cl. .................................. 250/343; 250/339; 356/246; 356/437; 356/440
[58] Field of Search ...................... 250/343, 345, 339; 356/418, 437, 440, 246

[56] References Cited

U.S. PATENT DOCUMENTS

| | | | |
|---|---|---|---|
| 2,279,143 | 4/1942 | Lohr | 84/404 |
| 2,729,143 | 1/1956 | White | 350/1.2 |
| 3,218,914 | 11/1965 | Bartz et al. | 356/320 |
| 3,588,496 | 6/1971 | Snowman | 250/343 |
| 3,661,462 | 5/1972 | Natens | 356/51 |
| 3,694,086 | 9/1972 | May | 356/51 |
| 4,063,816 | 12/1977 | Itoi et al. | 356/320 |
| 4,176,963 | 12/1979 | Fabinski et al. | 356/418 |
| 4,188,126 | 2/1980 | Boisde et al. | 356/440 |
| 4,205,913 | 6/1980 | Ehrfeld et al. | 356/72 |
| 4,209,232 | 6/1980 | Chernin | 350/619 |
| 4,254,336 | 3/1981 | Rostler | 250/294 |
| 4,322,621 | 3/1982 | Aagard | 250/343 |
| 4,577,105 | 3/1986 | Krempl et al. | 250/343 |
| 4,641,973 | 2/1987 | Nestler et al. | 356/418 |

FOREIGN PATENT DOCUMENTS 2303037  7/1974  Fed. Rep. of Germany ...... 250/343

OTHER PUBLICATIONS

"Dew Point Moisture Monitor Detector Head; Operation and Maintenance Manual" *Gulf Electronic Systems,* San Diego, Calif., #E-115-242 (Jan. 1973).

*Primary Examiner*—Janice A. Howell
*Assistant Examiner*—Constantine Hannaher
*Attorney, Agent, or Firm*—Joseph S. Iandiorio; Brian M. Dingman

[57] ABSTRACT

An infrared trace element detection system including an optical cell into which the sample fluid to be examined is introduced and removed. Also introduced into the optical cell is a sample beam of infrared radiation in a first wavelength band which is significantly absorbed by the trace element and a second wavelength band which is not significantly absorbed by the trace element for passage through the optical cell through the sample fluid. The output intensities of the sample beam of radiation are selectively detected in the first and second wavelength bands. The intensities of a reference beam of the radiation are similarly detected in the first and second wavelength bands. The sensed output intensity of the sample beam in one of the first and second wavelength bands is normalized with respect to the other and similarly, the intensity of the reference beam of radiation in one of the first and second wavelength bands is normalized with respect to the other. The normalized sample beam intensity and normalized reference beam intensity are then compared to provide a signal from which the amount of trace element in the sample fluid can be determined.

23 Claims, 10 Drawing Sheets

INFRARED TRACE ELEMENT DETECTION SYSTEM

This invention was made with government support under contract number DE-AC02-83ER80085 awarded by the Department of Energy. The government has certain rights in this invention.

FIELD OF INVENTION

This invention relates to an infrared trace element detection system, and in particular to a system which compares the intensity in two different spectral bands of a sample beam, reflected a number of times through the sample, and a reference beam.

BACKGROUND OF INVENTION

Conventional measurement of trace elements in gas samples has presented a number of difficulties. For example, to detect the amount of water present in a sample of the helium coolant from a nuclear reactor, typically the helium sample is passed over a mirror which is cooled so that any water present in the gas condenses. Light is passed through the sample and directed at the mirror; as the water condenses a change in reflection indicates the amount of water present in the gas. However, the response time required to sense the water, particularly at very low concentrations, is relatively long. Additionally, the system is complex and requires considerable maintenance. Refrigeration is required, the mirror periodically becomes pitted and water must be removed from the mirror between tests making for low response time and repetition rate.

Infrared detectors may be employed to monitor humidity and other trace elements. In such systems radiation including a first wavelength band which is significantly absorbed by the trace element and a second wavelength band which is not significantly absorbed, is passed through a gas sample. The output intensities of the respective bands are compared to provide a measure of the concentration of the trace element in the sample. Problems arise, however, as the filters or other means for providing the individual wavelength bands of radiation age or become contaminated. This tends to cause variations in the measured values of the compared intensities that are not due to changes in concentration. To avoid erroneous concentration measurements frequent calibration is therefore required.

Further disadvantages are exhibited by optical cells which hold the sample gas for testing. For example, to accurately and continuously monitor the sample gas a smooth uninterrupted gas flow is desired in the area of the introduced beam of radiation. However, present techniques for introducing the sample gas into the optical cell tend to generate considerable turbulence and undesirable recirculation within the cell which inhibit a smooth uninterrupted flow and permit dirt and other contaminants to collect on the mirrors of the optical cell. This interferes with proper circulation of the sample gas and causes inaccurate concentration measurements.

SUMMARY OF INVENTION

It is therefore an object of this invention to provide an improved infrared trace element detection system.

It is a further object of this invention to provide an infrared trace element detection system which yields extremely accurate measurements and which exhibits an improved response time, particularly when monitoring relatively low-concentration samples.

It is a further object of this invention to provide an infrared trace element detection system which avoids detector drift and measurement errors caused by such drift without requiring frequent calibration.

It is a further object of this invention to provide an infrared trace element detection system which has a long life and low service requirements.

It is a further object of this invention to provide an infrared trace element detection system which employs rugged optics suitable for use in high pressure/high temperature environments such as nuclear reactors.

It is a further object of this invention to provide an infrared trace element detection system having a smooth uninterrupted flow of sample fluid in the area of the infrared beam to provide timely, rapid, continuous monitoring of the sample fluid and reduce contaminant buildup on the mirrors of the optical cell.

This invention results from a realization that the infrared detection of trace elements in a fluid sample may be accomplished with much less detector drift and resultant measurement error by normalizing the output intensity of the radiation in a first wavelength band which is substantially absorbed by the trace element and a second wavelength band which is not substantially absorbed by the trace element; normalizing the absorbed and nonabsorbed intensities of a second reference beam of the infrared radiation; and then comparing two normalized intensities. In this manner any error which is introduced by either the absorbing or nonabsorbing filter is introduced into both the sample and reference beams and therefore corrected when the normalized intensities of the respective beams are compared.

This invention results from the additional realization that accuracy and performance of an infrared trace element detection system may be enhanced even further by introducing sample fluid into the system through a construction of confronting orifices which rapidly replenishes the fluid in the beam path within the cell and reduces the collection of stagnant gas in the vicinity of the beam path.

This invention features an infrared trace element detection system which includes an optical cell and means for introducing to and removing from said optical cell a sample fluid to be examined. There are means for introducing to the optical cell a sample beam of infrared radiation in a first wavelength band which is significantly absorbed by the trace element and a second wavelength band which is not significantly absorbed by the trace element for passage through the optical cell through the sample fluid. There are means for selectively detecting in the first and second wavelength bands the output intensities of the sample beam of radiation from the optical cell and the intensities of a reference beam of the radiation. There are means, responsive to the means for selectively detecting, for normalizing the sensed output intensity of the sample beam in one of the first and second wavelength bands with respect to the other. Means, responsive to the means for selectively detecting, are also provided for normalizing the sensed intensity of the reference beam in one of the first and second wavelength bands with respect to the other. There are means for comparing the normalized output intensity and the normalized reference intensity and means, responsive to the means for comparing, for determining the amount of trace element in the sample fluid.

In a preferred embodiment the means for selectively detecting includes a single detector. The means for selectively detecting may include chopper means for selectively transmitting in the first and second wavelength bands the sample beam and reference beam. Such means may include chopper means having first and second filter means and means for driving the chopper means to pass the first and second filter means selectively through the sample and reference beams of infrared radiation. Preferably, the first and second filter means of the chopper device are driven through the output beam from the optical cell. Sensor means may be provided for sensing the location of the chopper device.

The means for normalizing the sensed sample beam output intensity may include means for dividing one of the sensed sample beam intensities by the other. The means for normalizing the detected reference beam intensity may include means for dividing one of the detected reference beam intensities by the other. The means for comparing the normalized sample beam intensity and the normalized reference beam intensity may include means for dividing one of the normalized intensities by the other. The means for determining may include means for retrieving a stored predetermined concentration of the trace element corresponding to the comparison parameter of the normalized output and normalized reference intensities.

Means may be provided for indicating the amount of trace element detected in the sample fluid and alarm means may be activated when the amount of trace element exceeds a predetermined level.

The means for introducing the sample preferably includes a plurality of substantially confronting orifices arranged on opposite sides of the optical cell. The optical cell may be contained within an elongate housing having forward and rearward ends. The housing may include sealing means for withstanding high gas sample pressures of, for example, up to 850 psi. The optical cell may include forward and rearward reflector means located proximate the forward and rearward ends, respectively, of the housing. The forward reflector means may include a single mirror and the rearward reflector means may include a pair of mirrors having spaced-apart centers of curvature. Typically, at least one of the reflector means is concave. The infrared radiation in the first and second wavelength bands is preferably introduced through and exits from the optical cell proximate the forward end of the housing. The optical cell may include a multiple reflection optical cell.

DISCLOSURE OF PREFERRED EMBODIMENT

Other objects, features and advantages will occur from the following description of a preferred embodiment and the accompanying drawings, in which.

Figure 1:
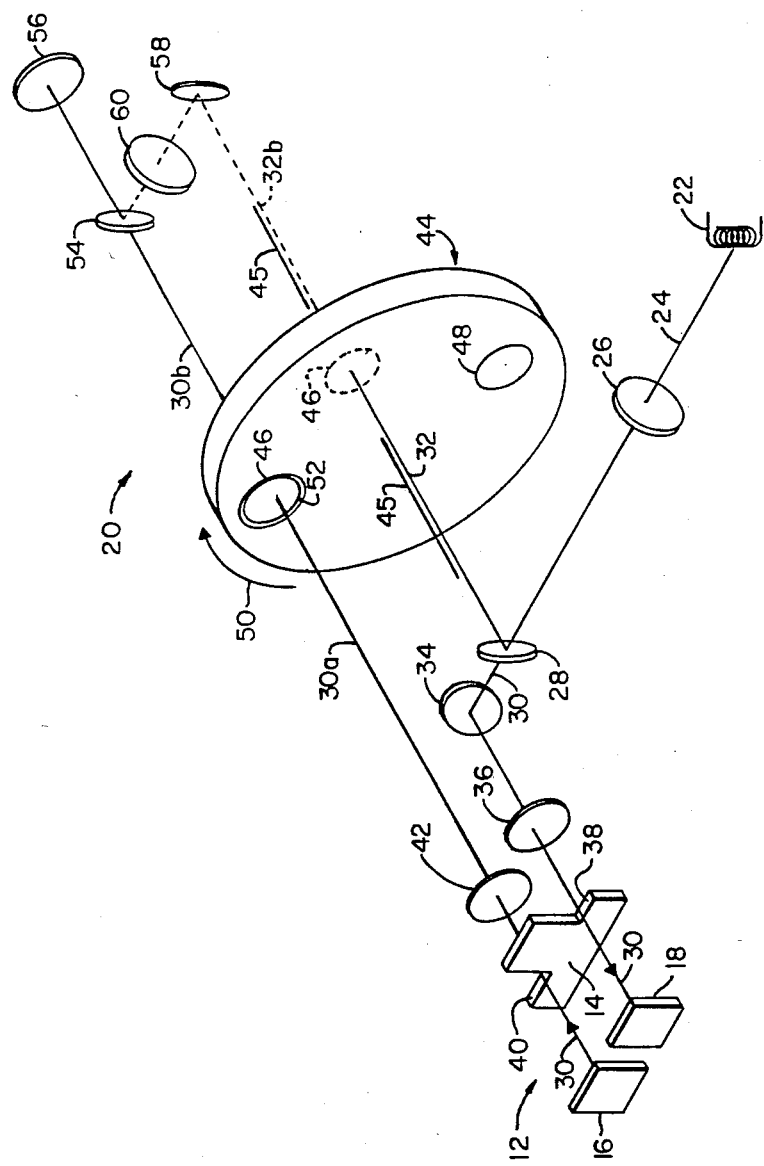
FIG. 1 is a simplified axonometric view of the optical elements of the infrared trace element detection system of this invention.

An infrared trace element detection system according to this invention may be accomplished using an optical cell. A preferred cell is a muliple reflection optical cell such as a White cell. Alternatively an optical cell which provides only a single reflecion or no reflections at all may be employed. A sample fluid, such as the helium coolant from a nuclear reactor, is introduced to and removed from the optical cell so that the sample may be monitored for the presence of water or other trace elements.

The multiple reflection optical cell receives a sample beam of infrared radiation including a first wavelength band which is significantly absorbed by the trace element and a second wavelength band which is not significantly absorbed by the trace element. The sample beam is reflected by the multiple reflection optical cell a number of times through the sample fluid. A preferred infrared source includes a resistively heated coil of wire, such as the Kanthal wire wound source manufactured by Infrared Industries, Inc., which provides a spectrally smooth broadband of radiation.

The output intensity of the sample beam of radiation from the multiple reflection optical unit as well as the intensity of a reference beam of the infrared radiation are selectively detected in the first and second wavelength bands. The selective detecting typically is accomplished with a chopper or other means for selectively transmitting in the first and second wavelength bands the sample beam and the reference beam. Although a separate chopper may be employed for each beam, it is preferred that a single chopper device having first and second filters be used for both beams. The chopper is driven to pass the first and second filters selectively through the sample and reference beams of radiation. For example, the chopper device may include a rotatably driven aluminum disk with narrow band filters located 180° apart. In monitoring a helium sample for the presence of water vapor a desirable infrared absorbing first band includes the wavelength 2.51–2.63 $\mu$m and the nonabsorbing second wavelength band may include the wavelengths 2.4–2.5 $\mu$m. Preferably, the first and second filters of the chopper device are driven through the output beam from the multiple reflection optical unit. Alternatively the sample beam may be chopped into alternating absorbing and nonabsorbing bands prior to introduction to the optical unit. It is preferred that a single detector be provided for both the sample and reference beams. However, each of those beams may employ a separate detector. Typically a lead sulfide detector or other suitable photodetector is employed.

The intensity of the sample beam in, typically, the first band is divided by, subtracted from or otherwise normalized with respect to the intensity in the second band. Similarly the sensed intensity of the reference beam in preferably the first wavelength band is divided by, subtracted from or otherwise normalized with respect to its sensed intensity in the second band. The normalized sample beam intensity and normalized reference beam intensity are then compared by division, subtraction or otherwise and a signal representative of this comparison parameter is used to determine the amount of trace element in the sample fluid. The amount of trace element may be calculated from the compared value. A sensor may be provided for sensing the location of the chopper so that the detected intensities may be processed in the proper sequence. Alternatively, the comparison parameter may be used to retrieve from a memory a corresponding value of the trace element.

The temperature and/or pressure of the sample fluid may also be sensed and used by a retrieval circuit or calculation circuit for determining the amount of the trace element in the sample at the sensed temperature and/or pressure. The determined amount may be indicated on, for example, a dial or readout, and if the trace element exceeds a predetermined amount an audio or visual alarm may be activated.

By dividing or otherwise comparing the normalized intensity of a sample beam with the normalized intensity of a reference beam the present invention overcomes the problem of instrument drift. If, for example, the filter which transmits the nonabsorbed wavelength band collects dirt or otherwise becomes contaminated at a rate different than the filter which transmits the absorbed wavelength band, the resulting changes in the normalized intensity in the first and second wavelength bands are exhibited by both the sample beam and the reference beam. Therefore, the compared value remains constant and the system remains calibrated.

This invention also features a fluid sample transmission system for introducing fluid sample into an optical cell such as the multiple reflection optical cell previously described. The sample is introduced through a plurality of substantially confronting orifices arranged on opposite sides of the optical cell. By "substantially confronting" it is meant that the opposing orifices may be either aligned or staggered relative to each other. Typically, the White cell or other optical cell used in this invention is contained within an elongate housing having forward and rearward ends. The multiple reflection optical unit includes forward and rearward reflector means located proximate the forward and rearward ends respectively of the housing. Typically, the forward reflector means includes a single mirror and the rearward reflector means includes a pair of mirrors having spaced apart centers of curvature. At least one of the reflectors may be concave. The sample beam of infrared radiation is preferably introduced to and exits from the multiple reflector optical cell proximate the forward end of the housing. The device may be arranged to permit one or many passes of the sample beam through the optical cell. Limiting the number of passes lessens degradation of the signal and simplifies reflector and detector alignment.

The substantially confronting orifices are arranged in the opposite sides of the optical unit so that fluid is introduced to the optical cell to create a smooth and uninterrupted flow in the area of the sample beam. This enables the sample fluid to be continuously circulated and monitored. Eddies which trap pockets of gas within the cell are reduced and contaminant buildup on the mirrors of the optical cell is lessened.

There is shown in FIG. 1 the optical elements of an infrared trace element detection system according to this invention. The sample fluid being monitored is introduced, as described more fully below, to a multiple reflection optical cell 12 which includes a forward mirror 14 and an opposing pair of spaced-apart concave rearward mirrors 16, 18 which face the front mirror. Although the embodiments discussed herein employ a multiple reflection cell, an optical cell employing only a single reflection or a single pass with no reflections may instead be used in the practice of the invention.

An infrared detection unit 20 features a source 22 of infrared radiation 24 including a first wavelength band which is significantly absorbed by the trace element being monitored in the sample fluid and a second wavelength band which is not significantly absorbed by the trace element. Radiation 24 is transmitted through lens 26 to a beam splitter 28 which splits the radiation into a sample beam 30 and a reference beam 32. Sample beam 30 is reflected from mirror 34 and introduced through window 36 to optical cell 12. Therein, beam 30 passes over shoulder 38 of mirror 14 and is reflected approximately 20 times between mirror 14 and rearward mirrors 16 and 18 respectively. Beam 30 finally exits cell 12 over shoulder 40 of mirror 14 and through window 42, and is projected from the cell as output beam 30a.

A chopper wheel 44, rotatable about axis 45, selectively transmits both output beam 30a and reference beam 32 in the first absorbing and second nonabsorbing wavelength bands. Chopper 44 includes a first filter 46 which transmits only radiation in the first band and a second filter 48, diametrically opposed to filter 46, which transmits only radiation in the second band. Chopper wheel 44 is rotated in the direction of arrow 50 so that filters 46 and 48 are alternately passed through both sample output beam 30a and reference beam 32. For example, first filter 46 is shown passing through output beam 30a. This causes radiation in the first absorbing wavelength band to be transmitted through the filter and through a lens 52 disposed behind the chopper wheel. Radiation 30b in the first wavelength band is then transmitted through beam splitter 54 and sensed by detector 56. As this occurs, chopper wheel 44 blocks transmission of reference beam 32 and, as a result, the intensity of that beam is not measured.

The chopper wheel continues rotating and after one-quarter turn first filter 46 is at the position indicated in phantom. The first wavelength band of the reference beam is then transmitted through filter 46. The transmitted portion 32b of the reference beam is reflected from mirror 58 and directed through lens 60 to beam splitter 54 where it is reflected and measured by detector 56. At the same time, transmission of the sample output beam 30a is blocked by chopper 44 and as a result only the intensity of the reference beam in the first wavelength band is measured.

An additional one-quarter turn places filter 48 in the path of sample output beam 30a. Accordingly, the second nonabsorbing wavelength band of the sample beam is transmitted through the chopper and sensed by detector 56. Filter 48 is then rotated through the path of reference beam 32 so that the intensity of the reference beam in the second wavelength band may be similarly detected.

With each revolution of chopper 44 detector 56 successively senses the intensities of the sample output beam 30a and reference beam 32 in the first wavelength band and the intensities of the sample and reference beams in the second wavelength band. Between each quarter turn the sample and reference beams are both blocked by the chopper and no infrared intensity is detected.

Figure 2:
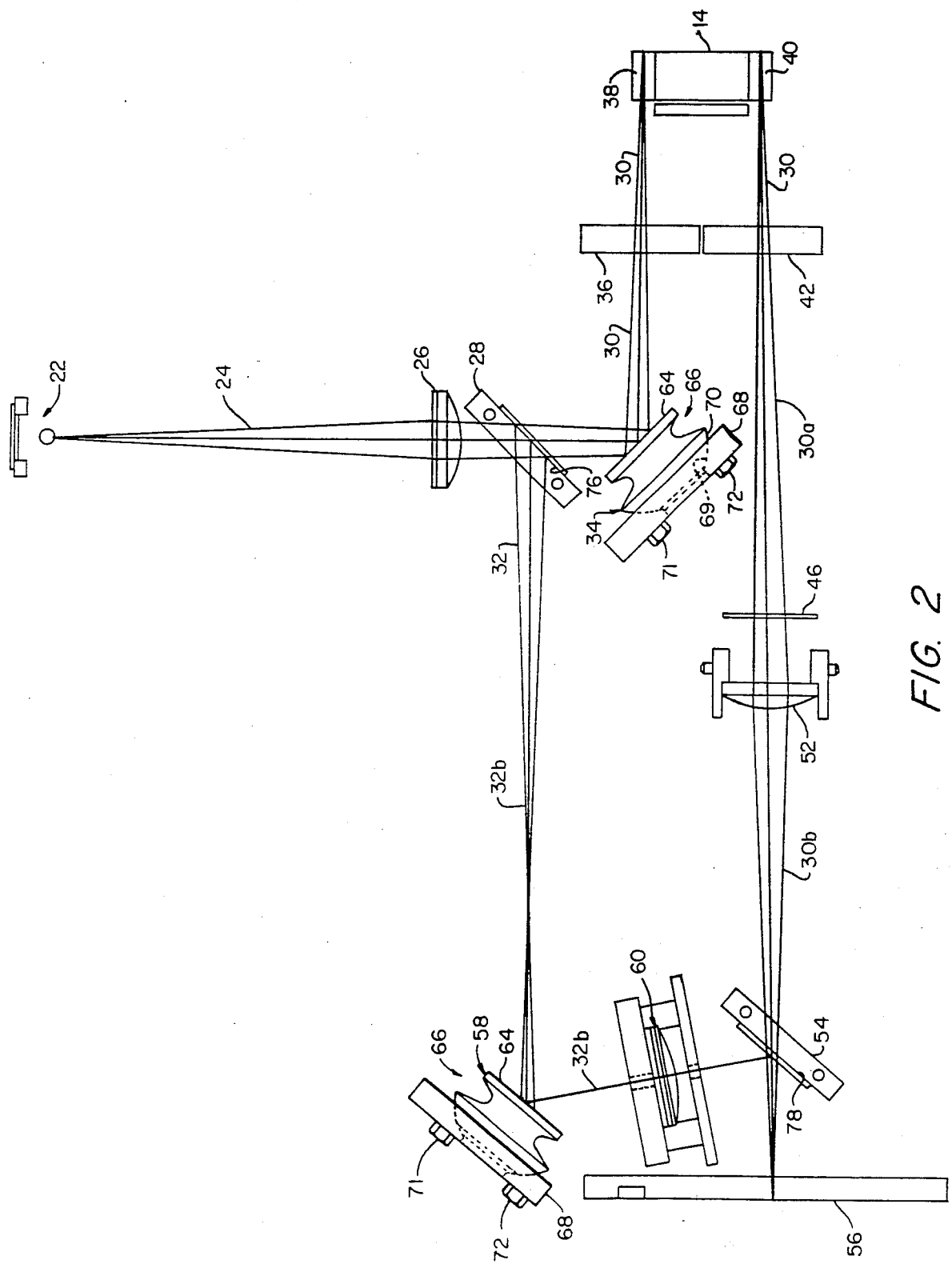
FIG. 2 is a simplified schematic view of certain of the optical elements of the detection system and the paths taken by the reference and sample beams.

The arrangement of the paths which the reference beam 32 and sample beam 30 travel are shown in somewhat more detail in plan view in FIG. 2. After leaving source 22 broadband radiation 24 passes through lens 26 and is split by beam splitter 28 into sample beam 30 and reference beam 32. Mirror 34 has a reflective surface 64 and is a part of a ball-and-socket mirror assembly 66. Assembly 66 includes a base 68 having a socket 69 which receives the circularly contoured bearing surfaces 70 of mirror 34. By adjusting screws 71 and 72 the angle of reflective surface 64 of mirror 34 may be set. In this manner the direction of sample beam 30 is adjusted to achieve the desired number of reflections within optical cell 12.

Sample beam 30 enters optical cell 12 through window 36 and passes over the respective shoulders 38 and 40 of mirror 14 as it enters and exits the optical cell. After exiting through window 42 of cell 12 sample output beam 30a encounters the rotating chopper wheel, not shown, and as the filters, e.g., filter 46, are alternately driven through the sample output beam, radiation is alternately transmitted in the selected first wavelength band and the second wavelength band. The transmitted wavelength band 30b passes through lens 52 which causes the beam to converge. This converging beam portion 30b is transmitted through beam splitter 54 and its intensity is sensed by detector 56.

Reference beam 32 is reflected from surface 76 of beam splitter 28 and the transmitted wavelength portion 32b is directed toward steering mirror 58. As with mirror 34, mirror 58 is included in a ball-and-socket mirror assembly 66 which enables the angle of reflective surface 64 of mirror 58 and therefore the direction of reflected reference beam portion 32b to be adjusted by adjusting screws 71 and 72. Reference beam portion 32b is reflected from the surface 64 of mirror 58 through lens 60. The beam is then reflected from front surface 78 of beam splitter 54 onto detector 56 which measures the intensity of the reference beam portion 32b transmitted by the chopper.

Figure 3:
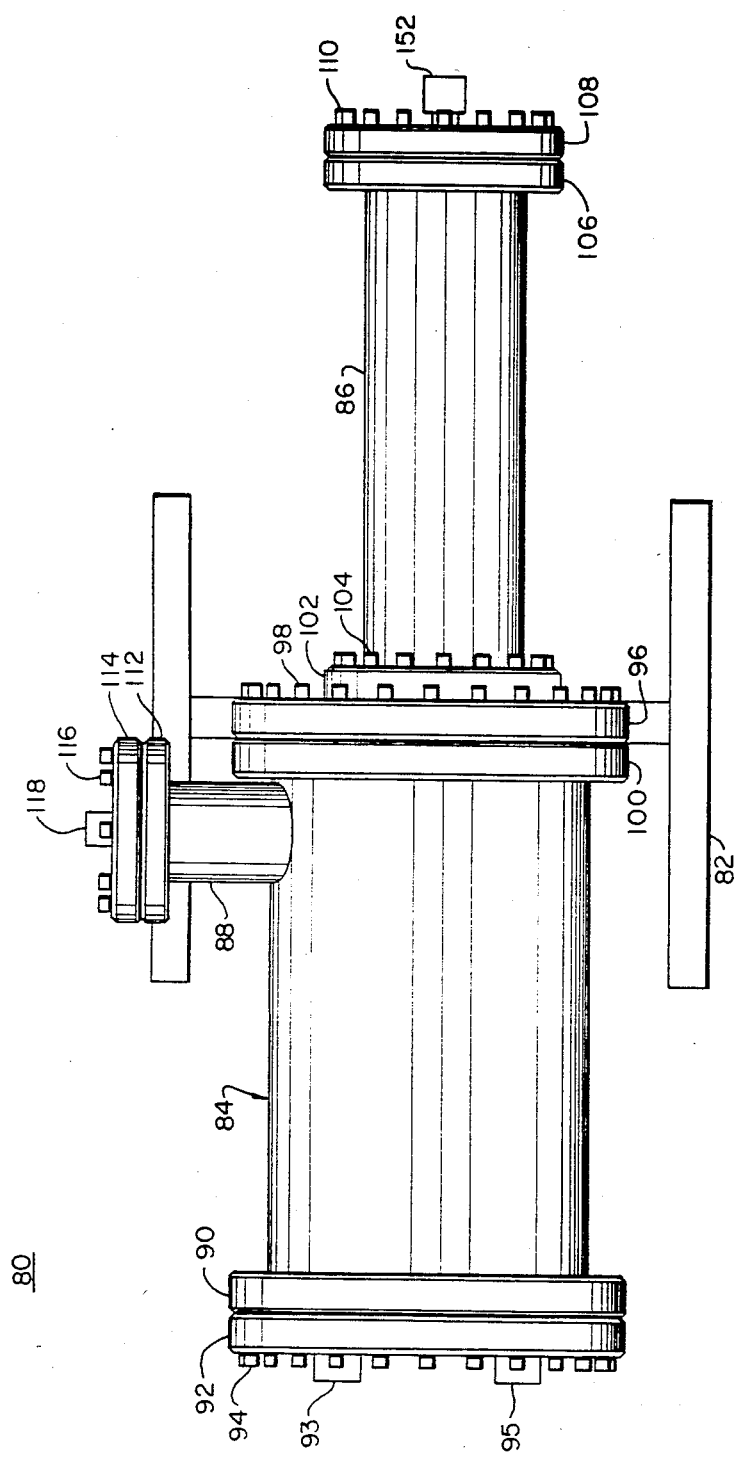
FIG. 3 is a top view of the trace element detection system housing.

A housing 80 for the infrared trace element detection system is shown in FIG. 3. The entire structure is mounted on a yoke 82 and includes a detector housing 84, an optical cell housing 86 and an infrared source housing 88. Detector housing 84 includes a flange 90 at one end to which a cover 92 is connected by bolts 94. A second flange 100 at the other end of housing 84 is similarly connected by bolts 98 to a flange 96 which also supports the optical components of FIGS. 1 and 2. Ports 93 and 95 are provided into housing 84 to conduct wiring from the detector to an external signal processor.

Optical cell housing 86 includes, at one end, a flange 102 which is attached to flange 96 by bolts 104. Typically, a high-pressure seal, not shown, such as a copper Varian gasket, is disposed between flange 102 and flange 96 to prevent leakage of sample fluid from the multiple reflection optical unit. The opposite end of housing 86 includes a flange 106 and end cover 108 which also may include a high pressure seal, effective for withstanding gas pressures of up to 850 psi, interposed between them. Flange 106 and cover 108 are secured together by bolts 110. Sample fluid is introduced, as described more fully below, through inlet 152.

Infrared source housing 88 includes a flange 112 and cover 114 which are connected by bolts 116. A port 118 conducts wiring connected to the infrared radiation source.

Figure 4:
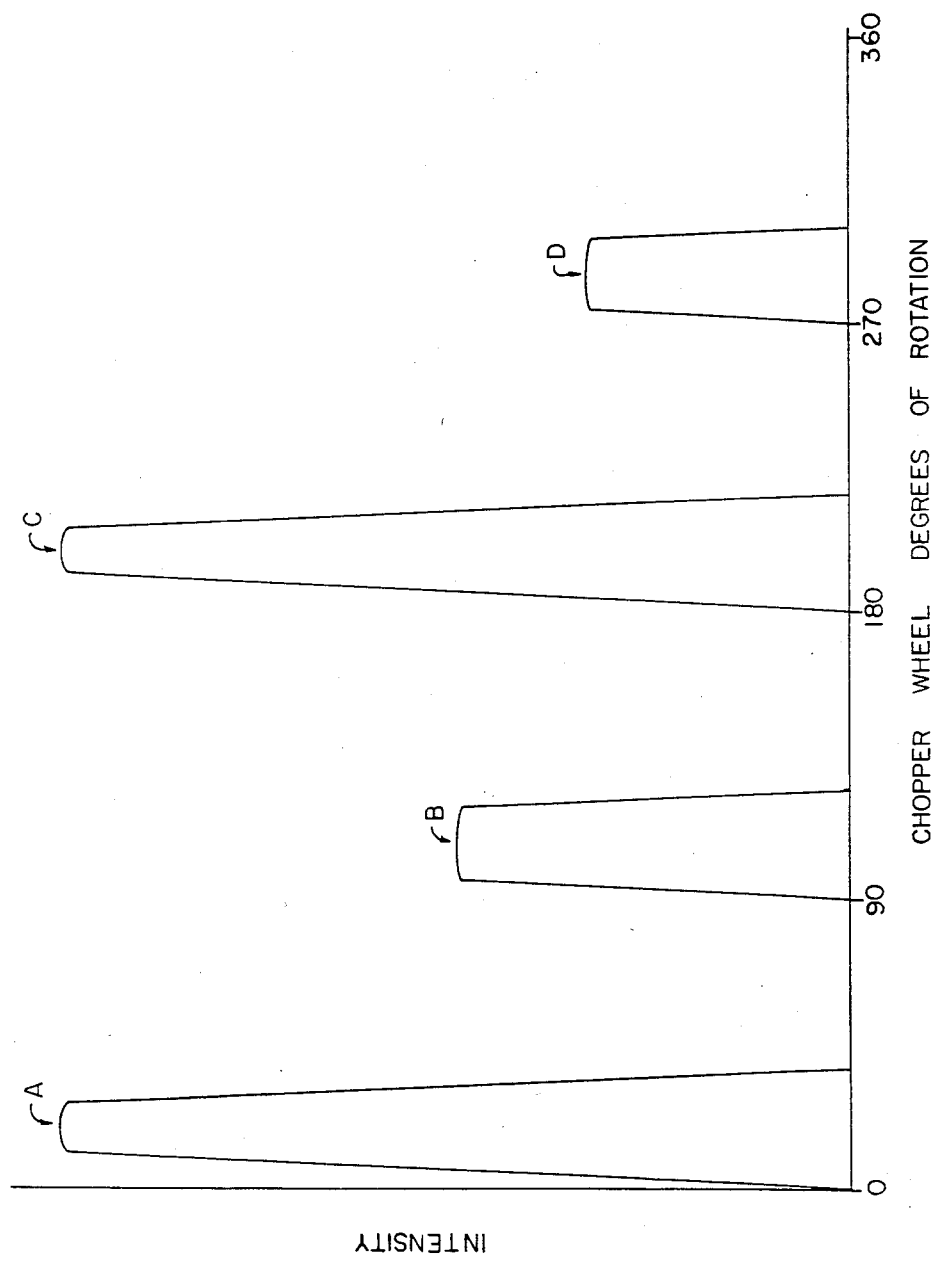
FIG. 4 is a graph illustrating the detected output and reference intensities versus the position of the chopper device.

The intensity measured by the detector during the course of a single representative rotation of the chopper wheel is shown in FIG. 4. For example, with first filter 46 at 0° (i.e., passing through sample output beam 30a as shown in FIG. 1) the intensity A of the sample output beam from the multiple reflection optical cell 12 in the first (absorbing) wavelength band is measured. The chopper then rotates 90° so that filter 46 is in the position shown in phantom in FIG. 1. The absorbing wavelength band of the reference beam 32 is thereby transmitted through filter 46 and its intensity B, FIG. 4, is measured.

At the 180° position the second filter 48 is passed through sample output beam 30a, the second (nonabsorbing) wavelength band of this beam is transmitted through the filter and its intensity C, FIG. 4, is sensed by the detector. A further rotation of 90° of the chopper wheel (i.e., at the 270° position) places the second filter 48 in the path of reference beam 32. As a result, the nonabsorbing wavelength band of the reference beam is transmitted and its intensity D is measured by the detector.

As indicated in FIG. 4, in the intervals between filters 46 and 48 the chopper wheel completely blocks the passage of the sample and reference beams. No infrared radiation is transmitted and the measured intensity is zero.

Figure 5:
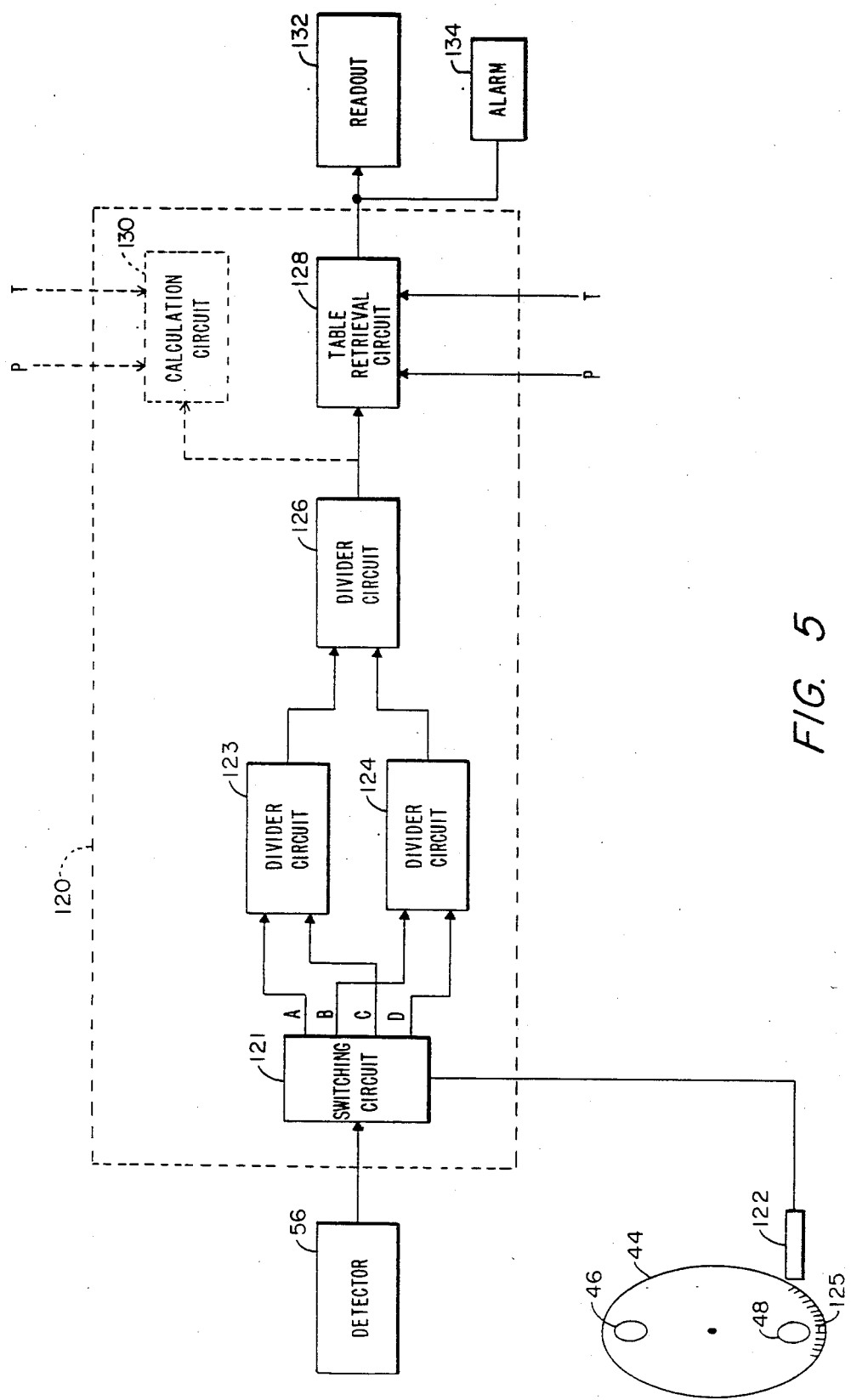
FIG. 5 is a schematic view of signal processor for normalizing and comparing the sensed detector intensities and for determining the trace element concentration and a circuit for sensing the location of the chopper device.

A signal processor 120 for processing the detected intensity signals A, B, C, and D is shown in FIG. 5. The respective signals are provided from detector 56 to a switching circuit 121. A sensor 122 detects appropriate indicia 125 disposed around the circumference of wheel 44, and provides a signal to circuit 121 which identifies the signal received from detector 56 as either signal A, B, C or D. The switching circuit feeds signals A and C, representing the intensities of the sample output beam in the absorbing and nonabsorbing wavelength bands respectively, to divider circuit 123 where they are divided to provide normalized signal A/C. Similarly, signals B and D, representing the intensities of the reference beam in the absorbing and nonabsorbing wavelength bands, respectively, are provided by switching circuit 121 to a divider circuit 124 where they are divided to yield the normalized signal B/D. Signals A/C and B/D are divided in divider circuit 126 to yield signal R (e.g., $(A \times D)/(B \times C)$). Signal R is provided along with signals indicative of the temperature T and the pressure P of the fluid sample to a table retrieval circuit 128 where the proportion of water or other trace element being measured in the sample is retrieved from calibration curves, described more fully in connection with FIG. 6, which are stored in the memory of the circuit. Alternatively, the proportion of trace element in the fluid sample may be determined by entering signal R into a calculation circuit 130 where a conventional algorithm is employed to calculate the proportion as described in connection with FIG. 7. The determined concentration of trace element is indicated on a readout 132 and if the proportion reaches an undesirably high level, an alarm 134 is activated.

A sensor is not required if the filters are arranged on the chopper at an interval other than 180°. For example, if they are separated by 135°, signals A, B, C, and D are provided at 0°, 90°, 135° and 225°, respectively. This uneven spacing serves to identify the respective signals and eliminates the need for a sensor.

Figure 6:
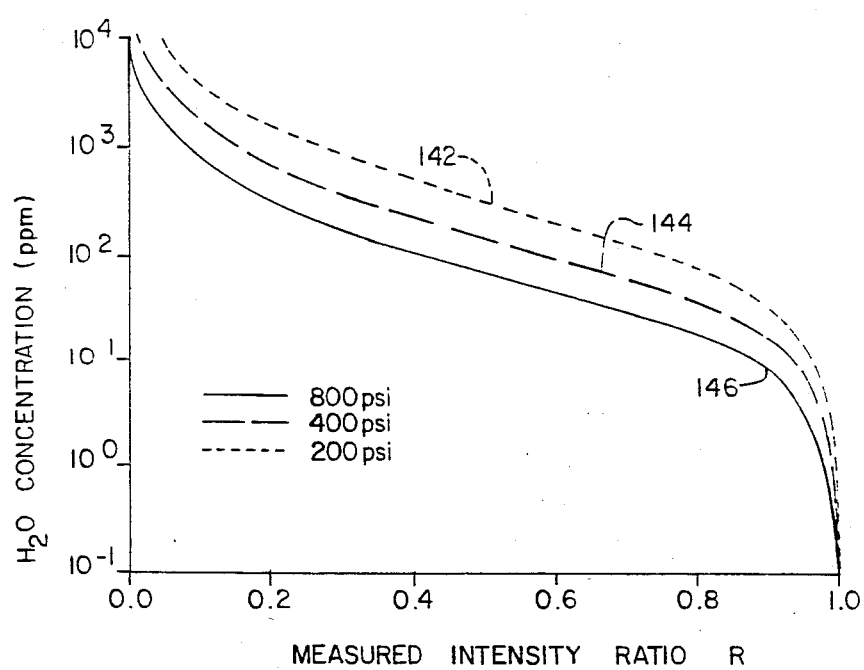
FIG. 6 is a graph illustrating curves representing the measured concentration of water versus the ratio of the normalized detector intensities at various pressures.

A calibration curve, FIG. 6, may be used by table retrieval circuit 128 for determining stored water proportion values for a sample of high-pressure helium. Values along the x axis represent the divider circuit output signal R provided to the retrieval circuit 128. Values along the y axis indicate the concentration of water in the helium sample in parts per million. Curve 142 indicates the calibrated concentration values at a pressure of 200 psi; curve 144 indicates such values at 400 psi; and curve 146 indicates the concentrations at 800 psi. These values are obtained in a helium sample which is maintained at a constant temperature of 110° F. Similarly shaped curves with different concentrations are obtained at different temperatures. Each of these calibrated curves is compiled by employing a helium sample having known concentrations of water and predetermined temperatures and pressures and measuring the values R for such samples.

Figure 7:
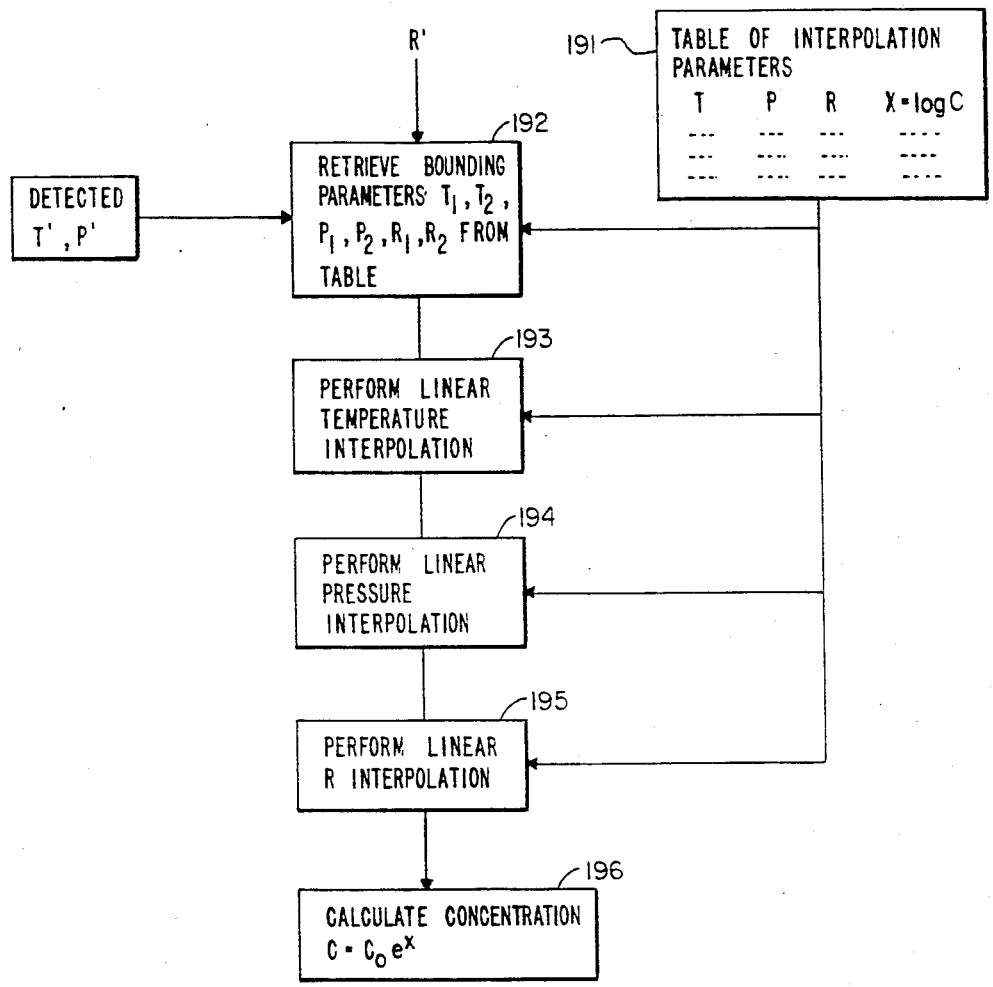
FIG. 7 is a flow chart for resolving the proportion of trace element in the sample gas.

Preferably logic may be employed in circuit 130 to calculate the proportion of trace element is shown in FIG. 7. Table 191 is provided with known combinations of values of temperature T, pressure P, ratio R and X, where X, a function of T, P and R, equals the log of the concentrations C. Table 191 thus expresses the functional dependence of X on T, P and R. Known temperatures, pressures and R values $T_1$, $T_2$, $P_1$, $P_2$ and $R_1$, $R_2$ which bound the detected values T', P' and R', respectively, are retrieved from Table 191, step 192. These values are used to perform known three dimensional linear interpolation, steps 193, 194 and 195 to calculate the value of X which is associated with T', P' and R'. Concentration is calculated, step 196, by re-exponentiating X and multiplying $e^x$ by $C_o$ where $C_o$ is a typically constant predetermined scaling factor.

Figure 8:
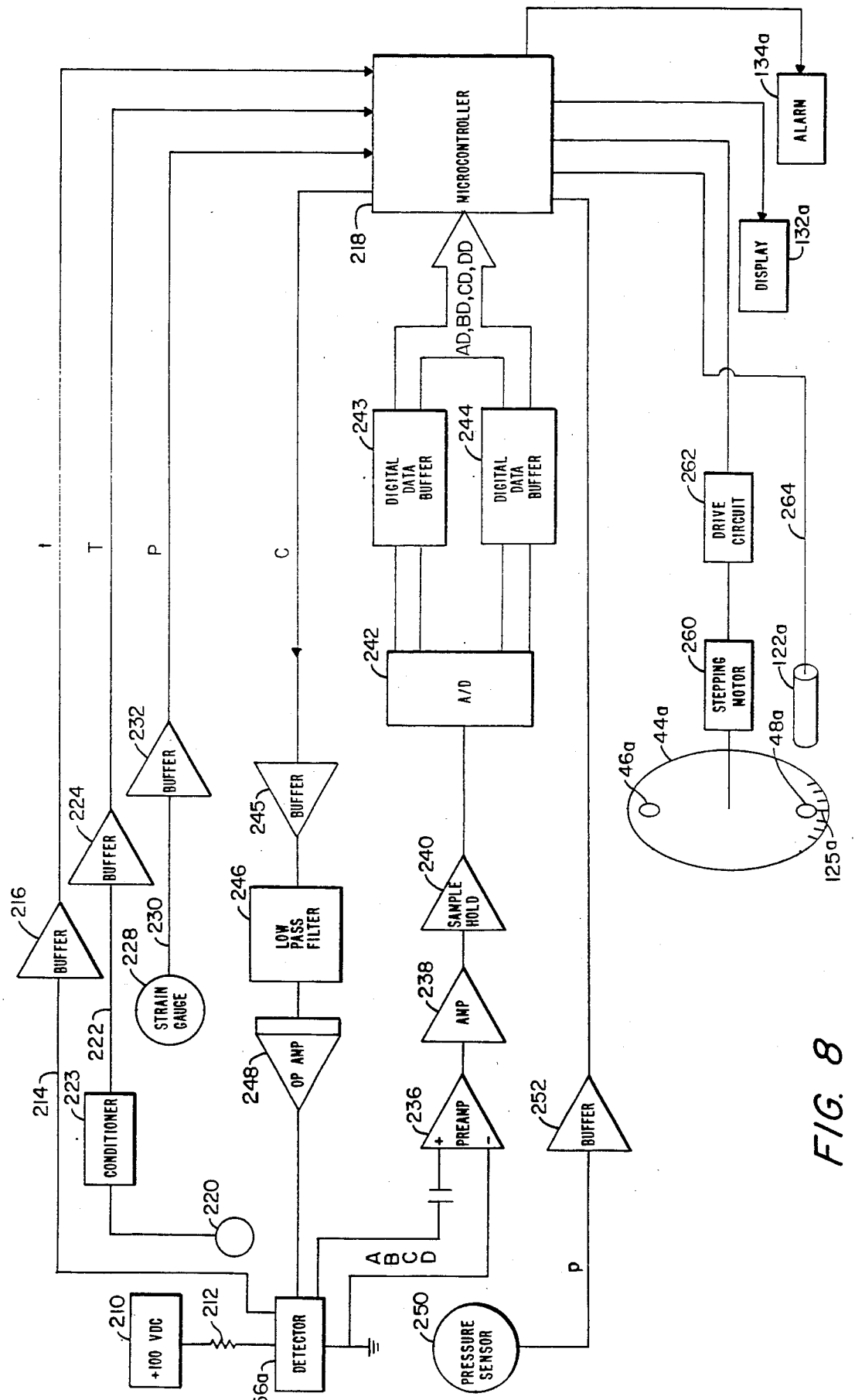
FIG. 8 is a schematic diagram of a preferred alternative signal processor which digitally processes the detected intensity signals to determine the proportion of trace element in the gas sample.

In an alternative preferred embodiment the intensity signals may be alternatively processed digitally as shown in FIG. 8. Detector 56a is connected to a 100-volt bias supply 210 through a resistor 212. Because the noise and sensitivity of detector 56a is strongly temperature dependent the detector includes a thermistor which provides a temperature signal t over line 214 and through amplifier 216 to microcontroller 218. A thermocouple 220 measures the temperature of the incoming high pressure gas entering optical cell 12, FIGS. 3, 9. Its signal T proceeds over line 222 through thermocouple signal conditioner 223 and amplifier 224 to microcontroller 218. A strain gauge 228 detects the pressure of the incoming gas sample and provides a signal P representative of that pressure over line 230 and through amplifier 232 to the microcontroller.

The absorption signals A, B, C and D provided by detector 56a are amplified and buffered by a preamp 236 and then directed through an amplifier 238, a sample and hold circuit 240 and an A/D converter 242. The signals are then transmitted through digital data buffers 243, 244 to the input of microcontroller 218. As a result each signal A-D is converted to a respective fourteen bit digital signal AD, BD, CD, DD.

The microcontroller is programmed in a conventional manner to process the signals so that signal AD is normalized with respect to signal CD, signal BD is normalized with respect to signal DD and the normalized intensity signals are compared to provide a signal R, not shown. The steps of such a program may include, for example, the division steps performed by the divider circuits described in FIG. 5. The signal R derived in this manner is then employed in either a table retrieval circuit or a calculation circuit in microcontroller 218, which operate analogously to the description in FIGS. 6 and 7 to provide the detected proportion of trace element to display 132a. Alarm 134a sounds when the concentration exceeds a predetermined level.

In order to prevent the heat generated by motor 260 and the ambient environment from disrupting the concentration determination the detector includes and is cooled by a solid state heat pump, not shown. Microcontroller 218 reads detector temperature t and feeds back a control signal C through buffer 245, low pass filter 246 and power operational amplifier 248 which operates the heat pump when the detector temperature t is too high.

Detector 56a and its associated optics are enclosed in a pressure vessel, housing 84, FIG. 3, which is sealed to prevent introduction of high pressure sample gas into the surrounding air through a leak or break in the windows 36 and 42. A second pressure sensor 250 monitors pressure in detector housing 84 and provides a signal p through buffer 252 to microcontroller 218. When that pressure exceeds a predetermined level an alarm, not shown, may be sounded.

Again, the sample and reference beams of infrared radiation are chopped into their respective wavelength bands by a chopper wheel 44. The wheel is driven by a stepper motor 260 which is controlled by the microcontroller through a drive circuit 262. Sensor 122a senses indicia 125a on the wheel and provides a signal to microcontroller 218 over line 264 which indicates to the microcontroller which signal AD-DD it is receiving.

Figure 9:
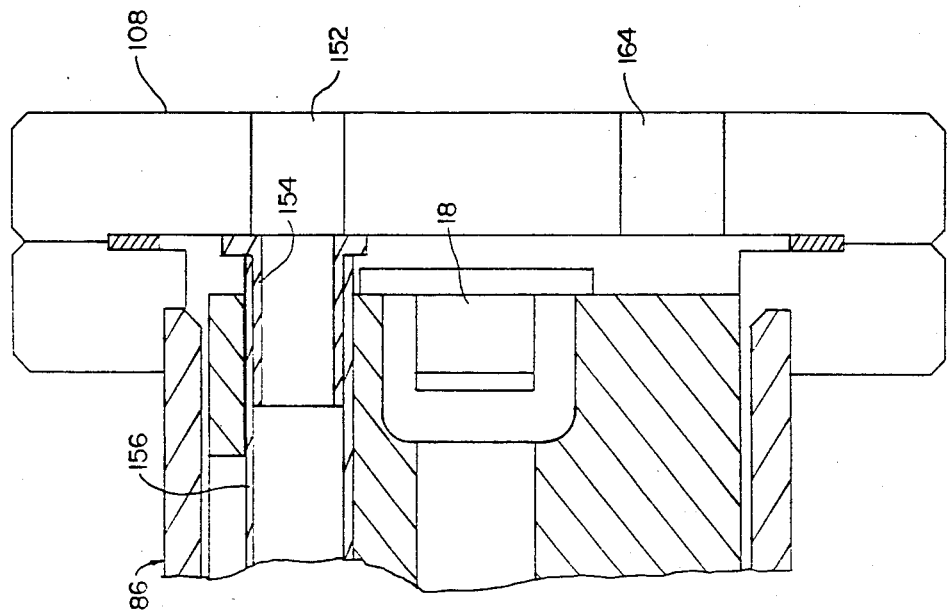
FIG. 9 is a side cross-sectional view of the optical cell and housing of FIG. 3.
Figure 9:
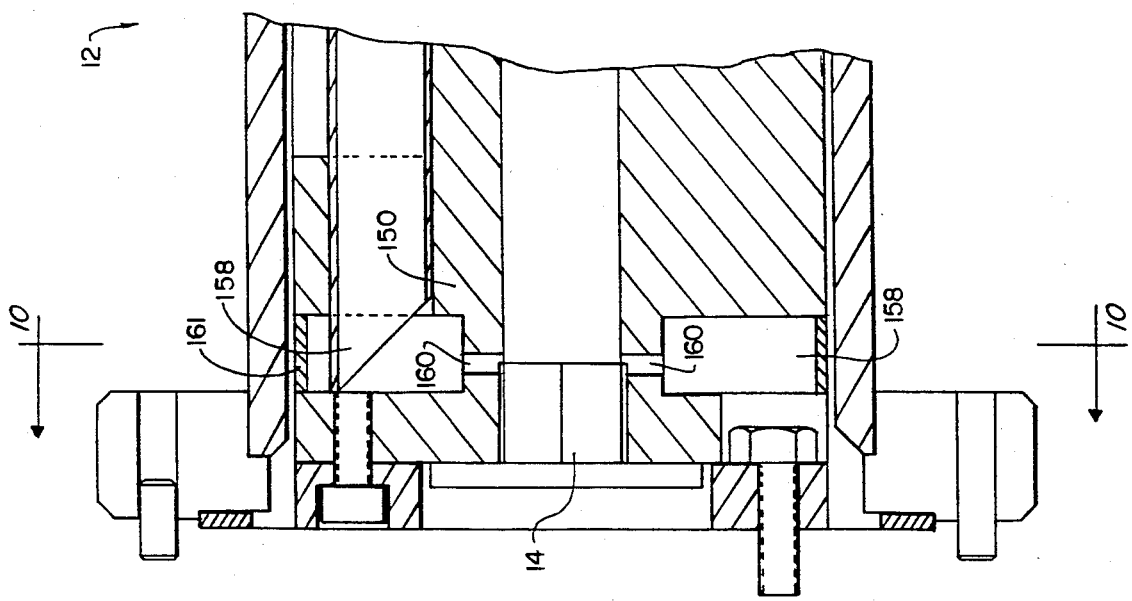
Figure 10:
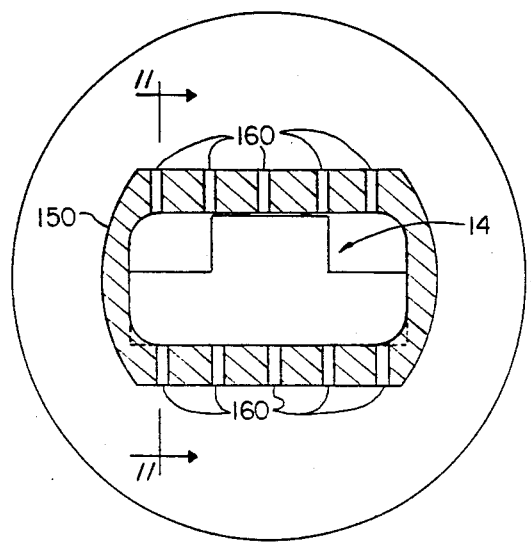
FIG. 10 is a cross-sectional view of the orifices for introducing sample fluid to the optical cell taken along line 10—10 of FIG. 11.
Figure 11:
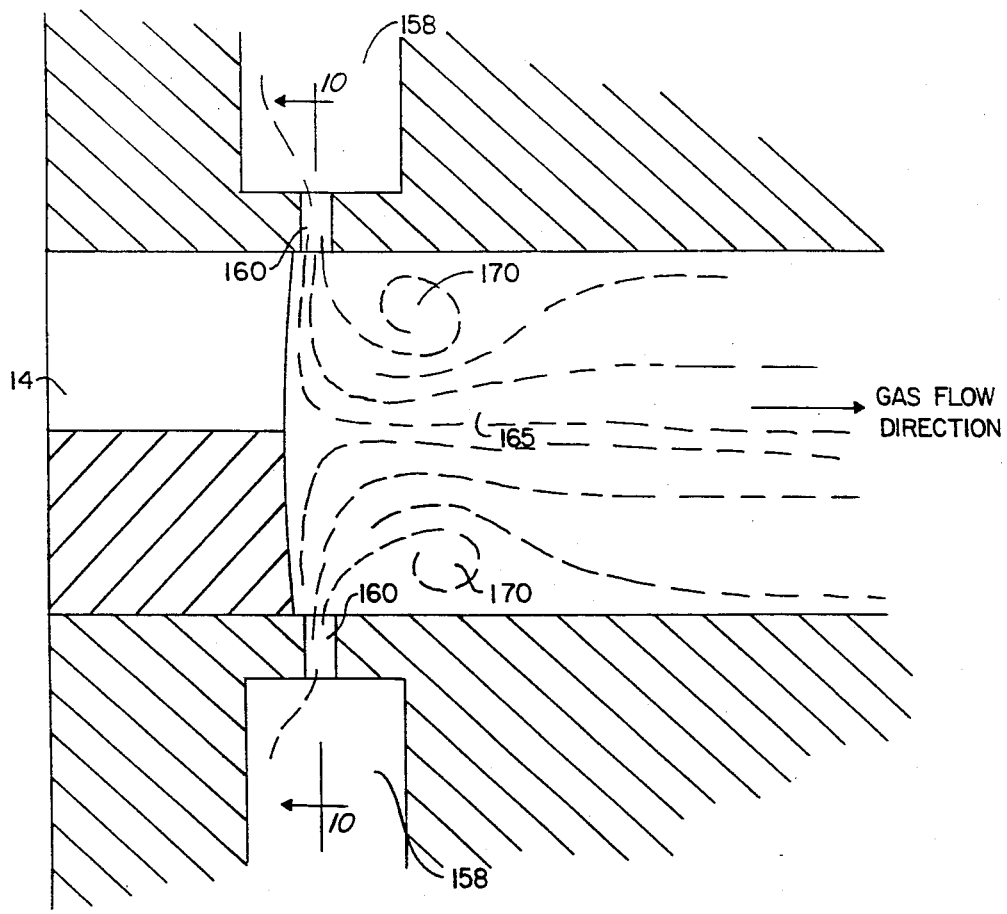
FIG. 11 is a cross-sectional view taken along line 11—11 of FIG. 10.

Sample fluid is introduced to and removed from optical cell 12 as shown in FIGS. 9-11. Optical cell 12, FIG. 9, includes a chamber 150 which extends generally from the forward end to the rearward end of housing portion 86. Forward mirror 14 and rearward mirrors 16 and 18 (only mirror 18 is shown) are mounted at opposite ends of chamber 150.

A fluid inlet 152 extends through cover 108 of housing portion 86 and communicates via nipple 154 with an elongate channel 156 that extends generally from the rearward end to the forward end of housing 86. An annular channel 158 is interconnected with elongate channel 156 and surrounds the forward end of optical chamber 150. A plurality of substantially confronting orifices 160 are connected to annular channel 158 and are arranged in opposite sides of optical chamber 150. An annular seal 161 is disposed peripherally about channel 158.

Sample fluid is introduced via inlet 152 and travels through channel 156 toward the forward end of the optical cell. The sample fluid is conducted through annular channel 158 and orifices 160 into the interior of optical chamber 150. Leakage from channel 158 is prevented by seal 161. The sample fluid travels through the chamber toward the rearward end of the cell, past mirrors 16 and 18 and exits the optical cell through outlet 164 which extends through cover 108 of housing 86.

Alternatively, the inlet may be provided proximate the top and the outlet proximate the bottom of the housing.

The opposing rows of orifices 160, FIG. 10, which are provided in both the upper and lower surfaces of chamber 150 immediately in front of the face of mirror 14 may be offset by, for example, 1/32 inch. This arrangement creates a smooth uninterrupted fluid flow 165, FIG. 11, in the area in which the sample beam is introduced into the optical cell. Introducing the sample fluid through the substantially confronting orifices 160 tends to disrupt and minimize the formation of eddies 170. This reduces the amount of stagnant sample fluid lingering in the vicinity of mirror 14. As a result, as the sample beam is introduced into the optical chamber, for example, past shoulder 40 of lens 14, and similarly as it is reflected back from the rearward mirrors toward the face of mirror 14, the beam encounters generally fresh sample fluid. This enhances the rapidity of the measurement of a change in trace element concentration. Additionally, since it is designed to reduce recirculation and stagnation of the introduced sample fluid, less dirt and dust collects on the surface of mirror 14.

In operation, sample fluid is introduced with reduced recirculation into optical cell 12 as shown in FIG. 11. Infrared radiation 24, FIGS. 1 and 2, is split into reference sample beam 30 and the sample beam is introduced into the optical cell where it undergoes multiple reflections. The sample output beam 30a and reference beam 32 are then chopped by chopper 44 so that at 90° intervals the intensities of the sample and reference beams in the first and second wavelength bands, respectively, are measured by detector 56. Those intensities A, B, C and D are fed to signal processor 120, FIG. 6, wherein the absorbed intensity of the sample beam is normalized relative to the nonabsorbed intensity by divider circuit 122. The absorbed intensity of the reference beam is similarly normalized with respect to the nonabsorbed intensity of the reference beam in divider circuit 124 and those respective ratios are compared in divider circuit 126 to yield a ratio signal R which compensates for filter contamination and detector errors. Signal R is then employed in a table retrieval circuit or calculation circuit to determine the amount of trace element in the sample fluid. That amount is indicated by readout 132 and if excessive amounts are indicated an alarm 134 is activated.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. An infrared trace element detection system comprising:
   an optical cell;
   means for introducing to and removing from said optical cell a sample fluid to be examined;
   means for introducing to said optical cell a sample beam of infrared radiation including a first wavelength band which is significantly absorbed by the trace element and a second wavelength band which is not significantly absorbed by the trace element for passage through said optical cell a number of times through the sample fluid;
   a detector for selectively detecting in said first and second wavelength bands the output intensities of said sample beam of radiation from said optical cell and the intensities of a reference beam of said radiation;
   means, responsive to said means for selectively detecting, for normalizing the sensed output intensity of the sample beam in one of said first and second wavelength bands with respect to the other; means, responsive to said means for selectively detecting, for normalizing the sensed intensity of the reference beam of radiation in one of said first and second wavelength bands with respect to the other;
   means for comparing the normalized output intensity and the normalized reference intensity; and
   means, responsive to said means for comparing, for determining the amount of trace element in the sample fluid.

2. The system of claim 1 in which said means for selectively detecting includes means for selectively transmitting in said first and second wavelength bands said sample beam and said reference beam.

3. The system of claim 2 in which said means for selectively transmitting includes chopper means having first filter means for transmitting light in said first wavelength band and second filter means for transmitting light in said second wavelength band and means for driving said chopper means to pass said first and second filter means selectively through said sample and reference beams of infrared radiation.

4. The system of claim 3 in which said first and second filter means of said chopper means are driven through the output beam from said optical cell.

5. The system of claim 3 further including sensor means for sensing the location of said chopper means.

6. The system of claim 1 in which said means for normalizing the sensed sample beam output intensity in one of said first and second wavelength bands with respect to the other includes means for dividing one of the sensed sample beam intensities by the other.

7. The system of claim 1 in which said means for normalizing the sensed reference beam intensity in one of said first and second wavelength bands with respect to the other includes means for dividing one of the detected reference beam intensities by the other.

8. The system of claim 1 in which said means for comparing the normalized sample beam intensities and the normalized reference intensities includes means for dividing one of the normalized intensities by the other.

9. The system of claim 1 in which said means for determining includes means for retrieving a stored predetermined concentration value of the trace element corresponding to the comparison parameter of the normalized sample and normalized reference beam intensities.

10. The system of claim 1 in which said means for introducing said sample includes a plurality of substantially confronting orifices arranged on opposite sides of said optical cell.

11. The system of claim 1 in which said optical cell is contained within an elongate housing having forward and rearward ends and includes forward and rearward reflector means located proximate said forward and rearward ends, respectively, of said housing.

12. The system of claim 11 in which said housing includes sealing means for withstanding high sample pressures.

13. The system of claim 12 in which said sealing means are capable of withstanding pressure of up to 850 psi.

14. The system of claim 11 in which said forward reflector means includes a single mirror.

15. The system of claim 11 in which said rearward reflector means includes a pair of mirrors with spaced-apart centers of curvature.

16. The system of claim 11 in which at least one of said reflector means is concave.

17. The system of claim 11 in which said infrared radiation in said first and second wavelength bands is introduced to and exits from said optical cell proximate the forward end of said housing.

18. The system of claim 1 further including means responsive to said means for determining for indicating the amount of trace element present in the sample fluid.

19. The system of claim 1 further including alarm means for indicating when the amount of trace element in the sample exceeds a predetermined level.

20. The system of claim 1 in which said optical cell includes a multiple reflection optical cell.

21. An infrared trace element detector for an optical cell containing a sample fluid to be examined comprising:

means for introducing to the optical cell a sample beam of infrared radiation including a first wavelength band which is significantly absorbed by the trace element and a second wavelength band which is not significantly absorbed by the trace element for passage through said optical cell through the sample fluid;

a detector means for selectively detecting in said first and second wavelength bands the output intensities of said sample beam of radiation from said optical cell and the intensities of a reference beam of said radiation;

means, responsive to said means for selectively detecting, for normalizing the sensed output intensity of the sample beam in one of said first and second wavelength bands with respect to the other;

means, responsive to said means for detecting, for normalizing the sensed intensity of the reference beam in one of said first and second wavelength bands with respect to the other; means for comparing the normalized sample beam intensity and the normalized reference beam intensities; and means, responsive to said means for comparing, for determining the amount of trace element in the sample fluid.

22. A fluid sample transmission system for an optical detection system comprising:

an optical cell for receiving a sample beam of radiation; and a plurality of substantially confronting orifices arranged in opposite sides of said optical cell for introducing sample fluid to said cell.

23. An infrared trace element detection system comprising:

an optical cell;

means for introducing to and removing from said optical cell a sample fluid to be examined including a plurality of substantially confronting orifices arranged in opposite sides of said optical cell;

means for introducing to said optical cell a sample beam of infrared radiation including a first wavelength band which is significantly absorbed by the trace element and a second wavelength band which is not significantly absorbed by the trace element for passage through said optical cell through the sample fluid;

a detector for selectively detecting in said first and second wavelength bands the output intensities of said sample beam of radiation from said optical cell and the intensities of a reference beam of said infrared radiation;

means responsive to said detector for normalizing the sensed output intensity of the sample beam in one of said first and second wavelength bands with respect to the other;

means responsive to said detector for normalizing the sensed intensity of the reference beam in one of said first and second wavelength bands with respect to the other; means for comparing the normalized sample beam intensity and the normalized reference beam intensity; and means responsive to said means for comparing for determining the amount of trace element in the sample fluid.

* * * * *